United States Patent [19]

Ratton

[11] Patent Number: 4,473,713

[45] Date of Patent: Sep. 25, 1984

[54] HYDROLYSIS OF ARYL-ALIPHATIC ETHERS

[75] Inventor: Serge Ratton, La Verpilliere, France

[73] Assignee: Rhone-Poulenc Specialites Chimiques, Courbevoie, France

[21] Appl. No.: 424,587

[22] Filed: Sep. 27, 1982

[30] Foreign Application Priority Data

Sep. 29, 1981 [FR] France ................... 81 18572

[51] Int. Cl.³ ............... C07C 37/055; C07C 45/61; C07C 39/00
[52] U.S. Cl. ................. 568/424; 568/433; 568/587; 568/650; 568/651; 568/653; 568/706; 568/709; 568/711; 568/735; 568/736; 568/743; 568/744; 568/773; 568/774; 568/780; 568/781; 568/805; 568/763; 568/766; 568/315; 260/465 F; 562/465; 560/55
[58] Field of Search ............. 568/805, 433, 735, 736, 568/773, 774, 780, 781, 744, 743, 706, 763, 766, 711, 709, 424, 587, 650, 653, 651, 315; 260/465 F; 562/465; 560/55

[56] References Cited

U.S. PATENT DOCUMENTS

| | | | |
|---|---|---|---|
| 561,077 | 6/1896 | Ach ......................... | 568/433 |
| 2,697,732 | 12/1954 | Mavity ..................... | 568/805 X |
| 3,256,336 | 6/1966 | Lange ....................... | 568/433 X |
| 3,367,972 | 2/1968 | Gitchel et al. ............ | 568/433 |

FOREIGN PATENT DOCUMENTS 646193  8/1962  Canada ......................... 568/433

OTHER PUBLICATIONS

Weggand-Hilgetag, Preparative Organic Chemistry (1972) 391-396.

Primary Examiner—Bernard Helfin
Attorney, Agent, or Firm—Burns, Doane, Swecker & Mathis

[57] ABSTRACT

At least one of the other functions comprising an aryl-aliphatic ether, e.g., veratrol, is catalytically hydrolyzed with water, e.g., to guaiacol, in the presence of a catalytically effective amount of a salt of a carboxylic acid.

10 Claims, No Drawings

HYDROLYSIS OF ARYL-ALIPHATIC ETHERS

BACKGROUND OF THE INVENTION

1. Field of the Invention The present invention relates to a novel process for the hydrolysis of at least one of the ether functions comprising certain aryl-aliphatic ethers.

2. Description of the Prior Art

U.S. Pat. No. 2,878,292 features the demethylation of vanillin with an agent such as hydrochloric, hydrobromic or hydriodic acid, aniline hydrochloride or ethanolamine hydrochloride, or the halides of aluminum, zinc, iron, tin, antimony and boron.

However, these demethylating agents are generally very corrosive to the process equipment, are ofttimes very expensive and frequently present awkward problems in the treatment of the final reaction compositions. Compare also U.S. Pat. Nos. 2,697,732 and 3,413,341; German Pat. No. 730,236.

SUMMARY OF THE INVENTION

Accordingly, a major object of the present invention is the provision of an improved process for the hydrolysis, with water, of at least one of the ether functions of certain aryl-aliphatic ethers, such hydrolysis being carried out in the presence of a catalytically effective amount of a salt of a carboxylic acid.

DETAILED DESCRIPTION OF THE INVENTION

More particularly according to this invention, advantageously hydrolyzed with water consistent herewith is at least one of the ether functions of an aryl-aliphatic ether having the structural formula (I):

$$R_1O\text{---}Ar\text{---}(R_2)_n \qquad (I)$$

in which Ar is benzene or naphthalene; $R_1$ is a linear or branched chain alkyl radical having from 1 to 4 carbon atoms, or a linear or branched chain alkenyl radical having 3 or 4 carbon atoms; and the substituents $R_2$, which may be identical or different, are each a hydroxyl group, an $OR_1$ radical, with $R_1$ being as abovedefined, a linear or branched chain alkyl radical having from 1 to 6 carbon atoms, a linear or branched chain alkenyl radical having from 2 to 6 carbon atoms, a phenyl radical optionally substituted with one or more alkyl radicals each having 1 to 4 carbon atoms, a cycloalkyl radical containing 5 or 6 atoms optionally substituted with one or more alkyl radicals each having 1 to 4 carbon atoms, a phenylalkyl radical, the aliphatic moiety of which containing from 1 to 4 carbon atoms, a cycloalkyl radical, the aliphatic moiety of which containing from 1 to 4 carbons, a halogen atom, a nitro group, an amino group, an aldehyde group —CHO, a nitrile group, a hydroxycarbonyl group, an acyl group having the formula —CO—$R_3$, in which $R_3$ is an alkyl radical having from 1 to 6 carbon atoms, a cycloalkyl radical containing 5 or 6 carbon atoms, optionally substituted with one or more alkyl radicals each having 1 to 4 carbon atoms, a phenyl radical optionally substituted with one or more alkyl radicals each having 1 to 4 carbon atoms, or a chain of a plurality of such radicals joined together by direct valence bonds, or an alkoxycarbonyl group having the formula —COOR$_4$, in which $R_4$ is an alkyl radical having from 1 to 6 carbon atoms, an alkenyl radical having from 2 to 6 carbon atoms, a cycloalkyl radical containing, 5 or 6 carbon atoms optionally substituted with one or more alkyl radicals each having 1 to 4 carbon atoms, a phenyl radical optionally substituted wich one or more alkyl radicals each having 1 to 4 carbon atoms, or a chain of a plurality of such radicals joined together by direct valence bonds; and n is an integer from 0 to 5, and said hydrolysis being characterized in that it is carried out in the presence of water and in the presence of a catalytically effective amount of a carboxylic acid salt.

The carboxylic acid salt which catalyzes the process according to the invention can be entirely a carboxylate which is stable under the working conditions of the process, especially a carboxylate of an alkali metal, of ammonium and of an alkaline earth metal. By way of example, carboxylates of sodium, potassium, lithium and ammonium are representative; the carboxylates of calcium, magnesium and barium are also exemplary. Carboxylates of alkali metals are, however, the preferred carboxylates.

The carboxylic acids employed for the preparation of the aforesaid carboxylates are advantageously monofunctional or polyfunctional, saturated or unsaturated, aliphatic acids, or are aromatic, aryl-aliphatic or cycloaliphatic carboxylic acids, the ring members of which can be substituted by one or more different substituents.

Exemplary of the aforesaid carboxylic acids, representative are the saturated aliphatic, monocarboxylic acids, such as acetic, propanoic, n-butanoic, 2-methyl-propanoic, n-pentanoic, 2-methyl-butanoic, 3-methyl-butanoic, 3,3-dimethyl-butanoic, n-hexanoic, 2-methyl-pentanoic, 3-methyl-pentanoic and 4-methyl-pentanoic acids; the unsaturated aliphatic monocarboxylic acids, such as propenoic, 2-butenoic, 2-methyl-propenoic, 3-butenoic, cis-2-methyl-2-butenoic (angelic), trans-2-methyl-2-butenoic (tiglic), 4-pentenoic, 3-hexenoic and 4-hexenoic acids; the saturated aliphatic dicarboxylic acids, such as malonic acid, succinic acid, glutaric acid and adipic acid; ethylenic dicarboxylic acids, such as maleic acid and fumaric acid, aromatic mono- or dicarboxylic acids, such as benzoic acid, ortho-phthalic acid, isophthalic acid, terephthalic acid, mononitrobenzoic acids and monochlorobenzoic acids; aryl-aliphatic carboxylic acids, such as phenylacetic acid, 2-phenyl-propanoic acids and 4-phenyl-propanoic acid; and cycloaliphatic carboxylic acids, such as 1,3-cyclohexanedicarboxylic acid and 1,4-cyclohexanedicarboxylic acid.

Among the carboxylates that are suitable according hereto, the salts of monofunctional saturated aliphatic carboxylic acids having from 2 to 6 carbon atoms, such as, in particular, acetic acid, propanoic, n-butanoic, n-pentanoic, n-hexanoic, 2-methyl-propanoic, 2-methyl-butanoic, 3-methyl-butanoic, 3,3-dimethylbutanoic, 2-methyl-pentanoic, 3-methyl-pentanoic and 4-methyl-pentanoic acids, or of difunctional saturated aliphatic carboxylic acids having from 3 to 6 carbon atoms, such as, in particular, malonic acid, succinic acid, glutaric acid and adipic acid, and the salts of benzoic acid and those of ortho-phthalic, isophthalic and terephthalic acids, are typically the preferred. Among the salts of these acids, the alkali metal salts are the preferred.

It is more especially preferred to use the sodium salts or potassium salts of the noted acids. Among these latter salts, sodium acetate, sodium propionate and sodium succinate are preferably employed.

The amount of carboxylic acid salt present in the reaction medium can vary over wide limits. If this amount is expressed relative to the starting material aryl-aliphatic ether, it is typically not less than 0.01 times the weight of said ether. The maximum amount is not critical. Usually, it does not exceed 50 times the weight of the ether. Most frequently, it is preferred to use weight ratio of carboxylic acid salt to aryl-aliphatic ether varying from 0.05 to 20.

The aryl-aliphatic ether starting materials according hereto are preferably compounds having the structural formula (I), in which: Ar is a benzene or naphthalene ring; $R_1$ is a linear or branched chain alkyl radical having from 1 to 4 carbon atoms, such as methyl, ethyl, isopropyl, n-propyl, n-butyl, isobutyl or tertiary butyl, a linear or branched chain alkenyl radical having 3 or 4 carbon atoms, such as allyl, propen-1-yl, isopropenyl, buten-1-yl, buten-2-yl, buten-3-yl, 1-methyl-propen-1-yl, 1-methyl-propen-2-yl, 2-methyl-propen-1-yl or 2-methyl-propen-2-yl, the substituents $R_2$, which may be identical or different, are each a hydroxyl group, a linear or branched chain alkyl radical having from 1 to 4 carbon atoms, such as those immediately above-indicated, a linear or branched chain alkenyl radical having from 2 to 4 carbon atoms, such as vinyl or one of those immediately above-indicated, an $OR_1$ radical, with $R_1$ being as above-defined, a phenyl radical optionally substituted with one or more alkyl radicals each having 1 to 4 carbon atoms, a cyclohexyl radical optionally substituted with one or more alkyl radicals each having 1 to 4 carbon atoms, a phenylalkyl radical, the aliphatic moiety of which containing from 1 to 3 carbon atoms, such as benzyl, phenylethyl, phenylpropyl and phenylisopropyl, a cyclohexylalkyl radical, the aliphatic moiety of which containing from 1 to 3 carbon atoms, a chlorine atom or a bromine atom, a nitro group, an aldehyde group, a hydroxycarbonyl group, a nitrile group, an acyl group having the formula —CO—$R_3$, in which $R_3$ is an alkyl radical having from 1 to 4 carbon atoms, a phenyl radical optionally substituted with one or more alkyl radicals each having 1 to 4 carbon atoms, a cyclohexyl radical optionally substituted with one or more alkyl radicals each having 1 to 4 carbon atoms, or a chain of a plurality of such radicals joined together by direct valence bonds, or an alkoxycarbonyl group having the formula —$COOR_4$, in which $R_4$ is an alkyl radical having from 1 to 4 carbon atoms, an alkenyl radical having from 2 to 4 carbon atoms, a phenyl radical optionally substituted with one or more alkyl radicals each having 1 to 4 carbon atoms, a cyclohexyl radical optionally substituted with one or more alkyl radicals each having 1 to 4 carbon atoms, or a chain of a plurality of such radicals joined together by direct valence bonds; and n is an integer from 0 to 3.

Exemplary of the aforedescribed aryl-aliphatic ethers, the following are representative:

Monoethers, such as anisole, ethoxybenzene (phenetole), butoxybenzene, isobutoxybenzene, 1-methoxynaphthalene, 2-ethoxynaphthalene, guaiacol, 3-methoxyphenol, 4-methoxyphenol, quaiethol, 3-ethoxyphenol, 4-ethoxyphenol, 2-chloroanisole, 3-chloroanisole, 4-chloroanisole, 2-bromoanisole, 3-bromoanisole, 4-bromoanisole, 2-nitroanisole, 3-nitroanisole, 4-nitroanisole, 2-methylanisole, 3-methylanisole, 4-methylanisole, 2-ethylanisole, 3-ethylanisole, 4-ethylanisole, 2-isopropylanisole, 3-isopropylanisole, 4-isopropylanisole, 2-propylanisole, 3-propylanisole, 4-propylanisole, 4-(propen-1-yl)anisole, 2-allylanisole, 4-allylanisole, 3-butylanisole, 4-butylanisole, 4-isobutylanisole, 2-tertiary butylanisole, 3-tertiary butylanisole, 4-tertiary butylanisole, 2-benzylanisole, 4-benzylanisole, 2-cyclohexylanisole, 1-bromo-2-ethoxybenzene, 1-bromo-3-ethoxybenzene, 1-bromo-4-ethoxybenzene, 1-chloro-2-ethoxybenzene, 1-chloro-3-ethoxybenzene, 1-chloro-4-ethoxybenzene, 1-ethoxy-2-nitrobenzene, 1-ethoxy-3-nitrobenzene, 1-ethoxy-4-nitrobenzene, 1-ethoxy-2-ethylbenzene, 1-ethoxy-3-ethylbenzene, 1-ethoxy-4-ethylbenzene, 2-methoxybenzaldehyde, 3-methoxybenzaldehyde, 4-methoxybenzaldehyde (para-anisaldehyde), 2-ethoxybenzaldehyde, 3-ethoxybenzaldehyde, 4-ethoxybenzaldehyde, 2,4-dichloroanisole, 2,4-dichloro-1-ethoxybenzene, 3-methoxypyrocatechol, 2-methoxyresorcinol, 5-methoxyresorcinol, 4-allyl-2-methoxyphenol, 2,3-dimethylanisole, 3,4-dimethylanisole, 2,4-dimethylanisole, 2,5-dimethylanisole, 2,3-dinitroanisole, 3,4-dinitroanisole, 3,5-dinitroanisole, 2,6-dinitroanisole, 2,4-dinitroanisole, 2,5-dinitroanisole, 1,3-dinitro-2-ethoxybenzene, 1,3-dinitro-5-ethoxybenzene, 1,4-dinitro-2-ethoxybenzene, 2,4-dinitro-1-ethoxybenzene, 3-chloro-2-nitroanisole, 4-chloro-2-nitroanisole, 3-ethoxy-2-hydroxybenzaldehyde, 3-ethoxy-4-hydroxybenzaldehyde, 4-ethoxy-2-hydroxybenzaldehyde, 5-ethoxy-2-hydroxybenzaldehyde, 2-hydroxy-3-methoxybenzaldehyde, 2-hydroxy-4-methoxybenzaldehyde, 3-hydroxy-4-methoxybenzaldehyde, 3-hydroxy-2-methoxybenzaldehyde, 4-hydroxy-3-methoxybenzaldehyde (vanillin), 5-bromovanillin, 5-chlorovanillin, 4-hydroxy-5-methoxy-2-nitrobenzaldehyde, and 5-hydroxy-4-methoxy-2-nitrobenzaldehyde; diethers, such as veratrole, 1,3-dimethoxybenzene, 1,4-dimethoxybenzene, 1,2-diethoxybenzene, 1,3-diethoxybenzene, 1,4-diethoxybenzene, 1,2-dipropoxybenzene, 1,3-dipropoxybenzene, 1,2-dimethoxy-3-nitrobenzene, 1,2-dimethoxy-4-nitrobenzene, 1,3-dimethoxy-2-nitrobenzene, 1,3-dimethoxy-5-nitrobenzene, 1,4-dimethoxy-2-nitrobenzene, 2,4-dimethoxy-1-nitrobenzene, 1-allyl-3,4-dimethoxybenzene, 1,4-dimethoxy-2-isopropylbenzene, 3,4-dimethoxybenzaldehyde, 4-ethoxy-3-methoxybenzaldehyde, 2,3-diethoxybenzaldehyde, 3,4-diethoxybenzaldehyde, 2,4-dimethoxybenzaldehyde, 1,2-dimethoxy-4,5-dinitrobenzene, 3,4-dimethoxy-6-hydroxybenzaldehyde, 2,6-dimethoxy-4-hydroxybenzaldehyde, 3,4-dimethoxy-5-hydroxybenzaldehyde and 3,5-dimethoxy-4-hydroxybenzaldehyde(syringaldehyde); and triethers, such as 1,2,3-trimethoxybenzene, 1,3,5-trimethoxybenzene, 1,2,4-trimethoxybenzene, 1,3,5-triethoxybenzene, 2,4,6-trimethoxybenzaldehyde and 3,4,5-trimethoxybenzaldehyde.

The hydrolysis according to the invention is preferentially carried out utilizing aryl-aliphatic ethers having the structural formula (I), in which Ar is a benzene ring; $R_1$ is a methyl radical; the substituents $R_2$, which may be identical or different, are each a hydroxyl group, a linear or branched chain alkyl radical having from 1 to 4 carbon atoms, a linear or branched chain alkenyl radical having from 2 to 4 carbon atoms, a methoxy group, a chlorine atom or bromine atom, a nitro group, or an aldehyde group; and n is an integer from 0 to 3.

The preferred starting material compounds according to the invention which are advantageously hydrolyzed are: veratrol, guaiacol, vanillin, 3-hydroxy-4-methoxybenzaldehyde, 3-hydroxy-2-methoxybenzaldehyde, 1,2,3-trimethoxybenzene, 1,3,5-trimethoxybenzene, 1,2,4-trimethoxybenzene, 2,4,6-trimethoxybenzaldehyde, 3,4,5-trimethoxybenzaldehyde, 1,3-dimethoxybenzene, 1,4-dimethoxybenzene, anisole, para-chloroanisole, ortho-chloroanisole, meta-chloroanisole, para-anisaldehyde, 2-methoxybenzaldehyde, 3-methoxybenzaldehyde, 3,5-dimethoxy-4-hydroxybenzaldehyde, 2,3-dimethoxybenzaldehyde, 3,4-dimethoxybenzaldehyde and 3,4-dimethoxy-5-hydroxybenzaldehyde.

Of course, the process according to the invention is equally applicable to individual aryl-aliphatic ethers and to mixtures of several aryl-aliphatic ethers.

The concentration of the aryl-aliphatic ethers in the reaction medium is not critical and also varies very widely. It is also possible to carry out the process undiluted, the ether being in the liquid state and the water then only playing the role of a reactant.

If the ether concentration is expressed in relation to the total reaction medium, the process is typically carried out utilizing from 1% to 90% by weight of ether. Most frequently, this concentration ranges from 2% to 80% by weight.

If it is desired to carry out the process with the ether at least partially in solution, and if the ether is sparingly soluble in water, its solubility can be enhanced by the addition of a water-miscible liquid solvent, in which the ether is soluble.

To carry out the process according to the invention, the reactants must be heated to reaction temperatures; such temperatures can vary from 150° C. to 350° C., and preferably range from 220° C. to 300° C.

Pressure is not a critical reaction parameter. Typically the process is carried out under autogenous pressure, obtained by heating the reaction mixture to the desired temperature in a suitable closed apparatus. It typically ranges from 10 bars to 100 bars. However, it may reach higher values, since it is possible, without departing from the scope of the invention, to establish an initial superatmospheric pressure in the cold apparatus, for example, by means of an inert gas, such as nitrogen.

The apparatus employed for the subject reaction is not specific to the process of the invention. It must simply possess certain characteristics, namely, it must be able to withstand the pressures attained on heating, it must be leakproof and, obviously, it must not be attacked by the reagents used.

In order to accelerate the kinetics of the hydrolysis reaction and thus to increase the degree of conversion for a given reaction time, it is advantageous to carry out the hydrolysis in the presence of a free carboxylic acid, which may conveniently be the acid corresponding to the carboxylate catalyst used.

The amount of free carboxylic acid used is not critical.

When the hydrolysis according to the invention is applied to a compound containing more than one ether group, it may be desirable to preferentially hydrolyze but a single ether group. In such event, it is useful to carry out the process in the presence of the aliphatic alcohol corresponding to the ether group. Thus, in the case of methyl ethers, methanol is introduced into the reaction medium.

The amount of alcohol thus added varies widely. The larger the amount of alcohol in relation to the ether, the more hydrolysis of only one ether group is favored relative to hydrolysis of all of the ether groups comprising the starting material ether.

In practice, the process according to the invention can be carried out in the following manner: the various components of the reaction mixture, as previously defined, are introduced into a suitable apparatus. The charge is heated to the desired temperature, preferably under stirring, although this is not truly indispensable, for a period that can vary, for example, from a few minutes to more than 20 hours. However, this period is generally on the order of a few hours, for example, 2 hours to 10 hours, depending upon the working temperature.

Upon completion of the reaction, the equipment is cooled and the final reaction composition is treated in conventional manner, depending upon the reagents used; the organic compounds other than the carboxylic acid salt are extracted utilizing a water-immiscible solvent.

The products obtained are separated off, especially from unconverted aryl-aliphatic ether, by the typical known procedures, and are then analyzed, if necessary, again by methods and techniques that are well known to this art.

The process according to the invention has very many possible applications, since it enables an ether group of an aromatic compound to be converted into a phenolic group.

It possesses the great advantage in that it can be applied to ethers in the presence of other compounds that are not etherified. Thus, it can be applied, for example, to veratrol, obtained by methylation of pyrocatechol according to the process described in French Patent Application No. 80/18,723 and containing unconverted pyrocatechol.

For example, it makes it possible, in particular, to obtain quaiacol, a compound used in the pharmaceutical industry and serving also as an intermediate in the synthesis of vanillin, from veratrol, a compound that currently has much fewer industrial applications.

In order to further illustrate the present invention and the advantages thereof, the following specific examples are given, it being understood that same are intended only as illustrative and in nowise limitative. Unless otherwise indicated, the analyses were carried out by gas-liquid chromatography.

EXAMPLE 1

The following reagents were introduced into suitable pressure-resistant glass tube:

| (i) | Anhydrous sodium acetate | 2.3 g |
| --- | --- | --- |
| (ii) | Acetic acid | 0.38 g |
| (iii) | Distilled water | 10 cm$^3$ |
| (iv) | Anisole | 2.0 g |

The tube was sealed and then heated, under agitation, to 250° C. and maintained at that temperature for 4 hours.

The final reaction mixture was colorless. It was cooled and was then treated with isopropyl ether. The unconverted anisole and the product phenol were determined.

The following were found:

Unconverted anisole: 1.871 g, or a degree of conversion (D.C.) of 6.5%;

Phenol formed: 0.113 g, or a yield in relation to the anisole converted (Y.C.) of 100%.

EXAMPLE 2

The procedure of Example 1 was repeated. The following reagents were introduced:

|     |                          |        |
| --- | ------------------------ | ------ |
| (i) | Anhydrous sodium acetate | 2.3 g |
| (ii) | Acetic acid | 0.38 g |
| (iii) | Distilled water | 8 cm³ |
| (iv) | Methanol | 2 cm³ |
| (v) | Anisole | 2.0 g |

The final reaction mixture was colorless. It was treated and analyzed as in Example 1.

|     |     |
| --- | --- |
| D.C. of anisol: | 6.7% |
| Y.C. of phenol: | 100% |

EXAMPLE 3

The procedure of Example 1 was repeated. The following reagents were introduced:

|     |                          |        |
| --- | ------------------------ | ------ |
| (i) | Anhydrous sodium acetate | 4.6 g |
| (ii) | Acetic acid | 0.38 g |
| (iii) | Distilled water | 10 cm³ |
| (iv) | Anisole | 2.0 g |

The final reaction mixture was colorless. It was treated and analyzed as in Example 1.

|     |     |
| --- | --- |
| D.C. of anisole: | 6.6% |
| Y.C. of phenol: | 100% |

EXAMPLE 4

The procedure of Example 1 was repeated. The following reagents were introduced:

|     |                          |        |
| --- | ------------------------ | ------ |
| (i) | Anhydrous sodium acetate | 2.3 g |
| (ii) | Acetic acid | 0.76 g |
| (iii) | Distilled water | 10 cm³ |
| (iv) | Anisole | 2.0 g |

The final reaction mixture was colorless. It was treated and analyzed as in Example 1.

|     |     |
| --- | --- |
| D.C. of anisole: | 8.1% |
| Y.C. of phenol: | 100% |

EXAMPLE 5

The procedure of Example 1 was repeated. The following reagents were introduced:

|     |                          |        |
| --- | ------------------------ | ------ |
| (i) | Anhydrous sodium acetate | 2.3 g |
| (ii) | Distilled water | 10 cm³ |
| (iii) | Anisole | 2.0 g |

The final reaction mixture was colorless. It was treated and analyzed as in Example 1.

|     |     |
| --- | --- |
| D.C. of anisole: | 6.3% |
| Y.C. of phenol: | 100% |

EXAMPLE 6

The procedure of Example 1 was repeated. The following reagents were introduced:

|     |                          |        |
| --- | ------------------------ | ------ |
| (i) | Anhydrous sodium acetate | 2.3 g |
| (ii) | Acetic acid | 0.38 g |
| (iii) | Distilled water | 10 cm³ |
| (iv) | Para-chloroanisole | 2.0 g |

The final reaction mixture was colorless. It was treated and analyzed as in Example 1.

|     |     |
| --- | --- |
| D.C. of para-chloroanisole: | 12.8% |
| Y.C. of para-chlorophenol: | 35% |

EXAMPLE 7

The procedure of Example 1 was repeated. The heating time at 250° was 2 hours instead of 4 hours. The following reagents were introduced:

|     |                          |        |
| --- | ------------------------ | ------ |
| (i) | Anhydrous sodium acetate | 2.3 g |
| (ii) | Acetic acid | 0.38 g |
| (iii) | Distilled water | 5 cm³ |
| (iv) | Methanol | 5 cm³ |
| (v) | Veratrol | 2.0 g |

The final reaction mixture was colorless. It was treated and analyzed as in Example 1.

|     |     |
| --- | --- |
| D.C. of veratrol: | 22.9% |
| Y.C. of guaiacol: | 90.0% |
| Y.C. of pyrocatechol: | 10.0% |

EXAMPLE 8

The procedure of Example 1 was repeated. The heating time at 250° was 5 hours instead of 4 hours. The following reagents were introduced:

|     |                          |        |
| --- | ------------------------ | ------ |
| (i) | Anhydrous sodium acetate | 2.3 g |
| (ii) | Acetic acid | 0.38 g |
| (iii) | Distilled water | 5 cm³ |
| (iv) | Methanol | 5 cm³ |
| (v) | Veratrol | 2.0 g |

The final reaction mixture was colorless. It was treated and analyzed as in Example 1:

|     |     |
| --- | --- |
| D.C. of veratrol: | 48.0% |
| Y.C. of guaiacol: | 75.0% |
| Y.C. of pyrocatechol: | 25% |

EXAMPLE 9

The procedure of Example 1 was repeated. The heating time at 250° was 2 hours instead of 4 hours. The following reagents were introduced:

|     |                          |        |
| --- | ------------------------ | ------ |
| (i) | Anhydrous sodium acetate | 2.3 g |
| (ii) | Acetic acid | 0.38 g |
| (iii) | Distilled water | 10 cm³ |

-continued

| (iv) | Veratrol | 2.0 g |

The final reaction mixture was colorless. It was treated and analyzed as in Example 1.

| D.C. of veratrol: | 22.6% |
| Y.C. of guaiacol: | 90.0% |
| Y.C. of pyrocatechol: | 10.0% |

EXAMPLE 10

The procedure of Example 1 was repeated. The heating time at 250° was 5 hours instead of 4 hours. The following reagents were introduced:

| (i) | Anhydrous sodium acetate | 2.3 g |
| (ii) | Acetic acid | 0.38 g |
| (iii) | Distilled water | 10 cm$^3$ |
| (iv) | Veratrol | 2.0 g |

The final reaction mixture was colorless. It was treated and analyzed as in Example 1.

| D.C. of veratrol: | 55.5% |
| Y.C. of guaiacol: | 63.0% |
| Y.C. of pyrocatechol: | 37.0% |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. The process which comprises hydrolyzing, under temperature and pressure conditions effective for hydrolysis, with water at least one of the ether functions of an aryl-aliphatic ether having the structural formula (I):

$$R_1O-Ar-(R_2)_n \quad (I)$$

in which Ar is benzene or naphthalene; $R_1$ is a linear or branched chain alkyl radical having from 1 to 4 carbon atoms, or a linear or branched chain alkenyl radical having 3 or 4 carbon atoms; the substituents $R_2$, which may be identical or different, are each a hydroxyl group, an $OR_1$ radical, with $R_1$ being as above-defined, a linear or branched chain alkyl radical having from 1 to 6 carbon atoms, a linear or branched chain alkenyl radical having from 2 to 6 carbon atoms, a phenyl radical optionally substituted with one or more alkyl radicals each having 1 to 4 carbon atoms, a cycloalkyl radical containing 5 or 6 carbon atoms optionally substituted with one or more alkyl radicals each having 1 to 4 carbon atoms, a phenylalkyl radical, the aliphatic moiety of which containing from 1 to 4 carbon atoms, a cycloalkyl radical, the aliphatic moiety of which containing from 1 to 4 carbon atoms, a halogen atom, a nitro group, an amino group, an aldehyde group —CHO, a nitrile group, a hydroxycarbonyl group, an acyl group having the formula —CO—$R_3$, in which $R_3$ is an alkyl radical having from 1 to 6 carbon atoms, a cycloalkyl radical containing 5 or 6 carbon atoms optionally substituted with one or more alkyl radicals each having 1 to 4 carbon atoms, a phenyl radical optionally substituted with one or more alkyl radicals each having 1 to 4 carbon atoms or a chain of a plurality of such radicals joined together by direct valence bonds, or an alkoxycarbonyl group having the formula —COOR$_4$, in which $R_4$ is an alkyl radical having from 1 to 6 carbon atoms, an alkenyl radical having from 2 to 6 carbon atoms, a cycloalkyl radical containing 5 or 6 carbon atoms, optionally substituted with one or more alkyl radicals each having 1 to 4 carbon atoms, a phenyl radical optionally substituted with one or more alkyl radicals each having 1 to 4 carbon atoms, or a chain of a plurality of such radicals joined together by direct valence bonds; and n is an integer from 0 to 5, in the presence of a catalytically effective amount of a salt of a carboxylic acid selected from the group consisting of alkali metal, ammonium, or alkaline earth metal salts of a carboxylic acid and mixtures thereof.

2. The process as defined by claim 1, wherein the carboxylic acid salt is an alkali metal carboxylate.

3. The process as defined by claim 1, wherein the carboxylic acid salt is a salt of a monofunctional saturated aliphatic carboxylic acid having from 2 to 6 carbon atoms, of a difunctional saturated aliphatic carboxylic acid having from 3 to 6 carbon atoms, of benzoic acid, or of ortho-, meta- or terephthalic acid.

4. The process as defined by claim 1, wherein said ether having the structural formula (I), Ar is benzene or naphthalene; $R_1$ is a linear or branched chain alkyl radical having from 1 to 4 carbon atoms, or a linear or branched chain alkenyl radical having 3 or 4 carbon atoms; the substituents $R_2$, which may be identical or different, are each a hydroxyl group, a linear or branched chain alkyl radical having from 1 to 4 carbon atoms, a linear or branched chain alkenyl radical having 2 to 4 carbon atoms, an $OR_1$ radical, with $R_1$ being as above-defined, a phenyl radical optionally substituted with one or more alkyl radicals each having 1 to 4 carbon atoms, a cyclohexyl radical optionally substituted with one or more alkyl radicals each having 1 to 4 carbon atoms, a phenyl alkyl radical, the aliphatic moiety of which containing from 1 to 3 carbon atoms, a cyclohexylalkyl radical, the aliphatic moiety of which containing from 1 to 3 carbon atoms, a chlorine atom or a bromine atom, a nitro group, an aldehyde group, a hydroxycarbonyl group, a nitrile group, an acyl group having the formula —CO—$R_3$, in which $R_3$ is an alkyl radical having from 1 to 4 carbon atoms, a phenyl radical optionally substituted with one or more alkyl radicals each having 1 to 4 carbon atoms, a cyclohexyl radical optionally substituted with one or more alkyl radicals each having 1 to 4 carbon atoms, or a chain of a plurality of such radicals joined together by direct valence bonds, or an alkoxycarbonyl group having the formula —COOR$_4$, in which $R_4$ is an alkyl radical having from 1 to 4 carbon atoms, an alkenyl radical having from 2 to 4 carbon atoms, a phenyl radical optionally substituted with one or more alkyl radicals each having 1 to 4 carbon atoms, a cyclohexyl radical optionally substituted with one or more alkyl radicals each having 1 to 4 carbon atoms, or a chain of a plurality of such radicals joined together by direct valence bonds; and n is an integer of from 0 to 3.

5. The process as defined by claim 4, wherein said ether having the structural formula (I), Ar is benzene; $R_1$ is methyl; the substituents $R_2$, which may be identical or different, are each a hydroxyl group, a linear or branched chain alkyl radical having from 1 to 4 carbon atoms, a linear or branched chain alkenyl radical having from 2 to 4 carbon atoms, a methoxy group, a chlorine atom or bromine atom, a nitro group, or an aldehyde group; and n is an integer from 0 to 3.

6. The process as defined by claim 1, the same being carried out at a temperature ranging from 150° C. to 350° C.

7. The process as defined by claim 6, the weight ratio of carboxylic acid salt present to the aryl-aliphatic ether ranging from 0.01 to 50.

8. The process as defined by claim 7, the same being carried out in the presence of free carboxylic acid.

9. The process as defined by claim 1, said aryl-aliphatic ether (I) having more than one ether function, and said hydrolysis being carried out in the presence of an alcohol corresponding to said more than one ether function, whereby but a single ether function is preferentially hydrolyzed.

10. The process as defined by claim 1, said aryl-aliphatic ether hydrolyzed being anisole, ethoxybenzene (phenetole), butoxybenzene, isobutoxybenzene, 1-methoxynaphthalene, 2-ethoxynaphthalene, guaiacol, 3-methoxyphenol, 4-methoxyphenol, guaiethol, 3-ethoxyphenol, 4-ethoxyphenol, 2-chloroanisole, 3-chloroanisole, 4-chloroanisole, 2-bromoanisole, 3-bromoanisole, 4-bromoanisole, 2-nitroanisole, 3-nitroanisole, 4-nitroanisole, 2-methylanisole, 3-methylanisole, 4-methylanisole, 2-ethylanisole, 3-ethylanisole, 4-ethylanisole, 2-isopropylanisole, 3-isopropylanisole, 4-isopropylanisole, 2-propylanisole, 3-propylanisole, 4-propylanisole, 4-(propen-1-yl)anisole, 2-allylanisole, 4-allylanisole, 3-butylanisole, 4-butylanisole, 4-isobutylanisole, 2-tertiary butylanisole, 3-tertiary butylanisole, 4-tertiary butylanisole, 2-benzylanisole, 4-benzylanisole, 2-cyclohexylanisole, 1-bromo-2-ethoxybenzene, 1-bromo-3-ethoxybenzene, 1-bromo-4-ethoxybenzene, 1-chloro-2-ethoxybenzene, 1-chloro-3-ethoxybenzene, 1-chloro-4-ethoxybenzene, 1-ethoxy-2-nitrobenzene, 1-ethoxy-3-nitrobenzene, 1-ethoxy-4-nitrobenzene, 1-ethoxy-2-ethylbenzene, 1-ethoxy-3-ethylbenzene, 1-ethoxy-4-ethylbenzene, 2-methoxybenzaldehyde, 3-methoxybenzaldehyde, 4-methoxybenzaldehyde (para-anisaldehyde), 2-ethoxybenzaldehyde, 3-ethoxybenzaldehyde, 4-ethoxybenzaldehyde, 2,4-dichloroanisole, 2,4-dichloro-1-ethoxybenzene, 3-methoxypyrocatechol, 2-methoxyresorcinol, 5-methoxyresorcinol, 4-allyl-2-methoxyphenol, 2,3-dimethylanisole, 3,4-dimethylanisole, 2,4-dimethylanisole, 2,5-dimethylanisole, 2,3-dinitroanisole, 3,4-dinitroanisole, 3,5-dinitroanisole, 2,6-dinitroanisole, 2,4-dinitroanisole, 2,5-dinitroanisole, 1,3-dinitro-2-ethoxybenzene, 1,3-dinitro-5-ethoxybenzene, 1,4-dinitro-2-ethoxybenzene, 2,4-dinitro-1-ethoxybenzene, 3-chloro-2-nitroanisole, 4-chloro-2-nitroanisole, 3-ethoxy-2-hydroxybenzaldehyde, 3-ethoxy-4-hydroxybenzaldehyde, 4-ethoxy-2-hydroxybenzaldehyde, 5-ethoxy-2-hydroxybenzaldehyde, 2-hydroxy-3-methoxybenzaldehyde, 2-hydroxy-4-methoxybenzaldehyde, 3-hydroxy-4-methoxybenzaldehyde, 3-hydroxy-2-methoxybenzaldehyde, 4-hydroxy-3-methoxybenzaldehyde (vanillin), 5-bromovanillin, 5-chlorovanillin, 4-hydroxy-5-methoxy-2-nitrobenzaldehyde, 5-hydroxy-4-methoxy-2-nitrobenzaldehyde, veratrole, 1,3-dimethoxybenzene, 1,4-dimethoxybenzene, 1,2-diethoxybenzene, 1,3-diethoxybenzene, 1,4-diethoxybenzene, 1,2-dipropoxybenzene, 1,3-dipropoxybenzene, 1,2-dimethoxy-3-nitrobenzene, 1,2-dimethoxy-4-nitrobenzene, 1,3-dimethoxy-2-nitrobenzene, 1,3-dimethoxy-5-nitrobenzene, 1,4-dimethoxy-2-nitrobenzene, 2,4-dimethoxy-1-nitrobenzene, 1-allyl-3,4-dimethoxybenzene, 1,4-dimethoxy-2-isopropylbenzene, 3,4-dimethoxybenzaldehyde, 4-ethoxy-3-methoxybenzaldehyde, 2,3-diethoxybenzaldehyde, 3,4-diethoxybenzaldehyde, 2,4-dimethoxybenzaldehyde, 1,2-dimethoxy-4,5-dinitrobenzene, 3,4-dimethoxy-6-hydroxybenzaldehyde, 2,6-dimethoxy-4-hydroxybenzaldehyde, 3,4-dimethoxy-5-hydroxybenzaldehyde, 3,5-dimethoxy-4-hydroxybenzaldehyde (syringaldehyde), 1,2,3-trimethoxybenzene, 1,3,5-trimethoxybenzene, 1,2,4-trimethoxybenzene, 1,3,5-triethoxybenzene, 2,4,6-trimethoxybenzaldehyde or 3,4,5-trimethoxybenzaldehyde.

* * * * *